(12) United States Patent
Michienzi (10) Patent No.: US 10,451,594 B2
(45) Date of Patent: Oct. 22, 2019

(54) LIQUID CHROMATOGRAPHY CONDUIT ASSEMBLIES HAVING HIGH PRESSURE SEALS

(75) Inventor: Joseph D. Michienzi, Plainville, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 333 days.

(21) Appl. No.: 14/233,212

(22) PCT Filed: Aug. 23, 2012

(86) PCT No.: PCT/US2012/051974
§ 371 (c)(1),
(2), (4) Date: Jan. 16, 2014

(87) PCT Pub. No.: WO2013/032833
PCT Pub. Date: Mar. 7, 2013

(65) Prior Publication Data
US 2014/0158599 A1 Jun. 12, 2014

Related U.S. Application Data

(60) Provisional application No. 61/527,648, filed on Aug. 26, 2011, provisional application No. 61/527,639, (Continued)

(51) Int. Cl.
*G01N 30/60* (2006.01)
*B01D 15/10* (2006.01)
(Continued)

(52) U.S. Cl.
CPC ......... *G01N 30/6026* (2013.01); *B01D 15/10* (2013.01); *B01D 15/22* (2013.01);
(Continued)

(58) Field of Classification Search
CPC .... B01D 15/10; B01D 15/1871; B01D 15/22; B05B 5/16; G01N 30/60; G01N 30/6004;
(Continued)

(56) References Cited

U.S. PATENT DOCUMENTS 4,116,836 A   9/1978   DeAngelis
5,044,190 A   9/1991   Hoff et al.
(Continued)

FOREIGN PATENT DOCUMENTS

EP   1399641 A1   3/2004
GB   2084063      4/1982
(Continued)

OTHER PUBLICATIONS

International Search Report and Written Opinion in related international patent application No. PCT/US12/1974, dated Nov. 16, 2012; 8 pages.
(Continued)

*Primary Examiner* — Benjamin L Lebron
(74) *Attorney, Agent, or Firm* — Schmeiser, Olsen & Watts LLP (57) ABSTRACT

Described is a tubing assembly which includes a permanently deformable outer tube, an intermediate tube and an inner tube. A radial seal is provided by a uniform radial crimp having a non-zero longitudinal length at a longitudinal location on the tubing assembly. In some embodiments one or both ends of the assembly have a uniform radial crimp and are polished so that the ends of two or more of the tubes are substantially flush with each other to thereby block the passage of fluids between the ends of the tubes. In other embodiments the uniform radial crimps are at other longitudinal locations where a high pressure seal is desired. The longitudinal length and the depth of each uniform radial crimp can be formed to accommodate the requirements of a
(Continued)

particular application so that leakage along the tubing assembly is prevented and void volume is reduced or eliminated.

12 Claims, 8 Drawing Sheets

Related U.S. Application Data filed on Aug. 26, 2011, provisional application No. 61/527,747, filed on Aug. 26, 2011, provisional application No. 61/527,638, filed on Aug. 26, 2011, provisional application No. 61/621,852, filed on Apr. 9, 2012.

(51) Int. Cl.
| | | |
|---|---|---|
| *B01D 15/22* | (2006.01) | |
| *B05B 5/16* | (2006.01) | |
| *G01N 30/72* | (2006.01) | |
| *B01D 15/18* | (2006.01) | |

(52) U.S. Cl.
CPC ............ *B05B 5/16* (2013.01); *G01N 30/60* (2013.01); *G01N 30/603* (2013.01); *G01N 30/6052* (2013.01); *B01D 15/1871* (2013.01); *G01N 30/6004* (2013.01); *G01N 30/6039* (2013.01); *G01N 30/6095* (2013.01); *G01N 30/7266* (2013.01); *Y10T 29/49908* (2015.01)

(58) Field of Classification Search
CPC ............ G01N 30/6026; G01N 30/603; G01N 30/6039; G01N 30/6052; G01N 30/6095; G01N 30/7266; Y10T 29/49908
See application file for complete search history.

(56) References Cited

U.S. PATENT DOCUMENTS

| | | | |
|---|---|---|---|
| 5,316,262 | A | 5/1994 | Bruce et al. |
| 5,651,885 | A | 7/1997 | Shick |
| 5,800,692 | A | 9/1998 | Naylor et al. |
| 6,039,084 | A | 3/2000 | Martucci et al. |
| 6,139,732 | A | 10/2000 | Pelletier |
| 6,629,350 | B2 * | 10/2003 | Motsenbocker ........ A61F 2/958 29/237 |
| 9,983,178 | B2 | 5/2018 | Michienzi et al. |
| 2003/0186566 | A1 | 10/2003 | Laub et al. |
| 2004/0035774 | A1 | 2/2004 | Horman et al. |
| 2005/0092182 | A1 | 5/2005 | Thielen et al. |
| 2006/0016499 | A1 | 1/2006 | Blanchard et al. |
| 2007/0068872 | A1 | 3/2007 | Gerhardt et al. |
| 2007/0138076 | A1 | 6/2007 | Daridon et al. |
| 2009/0257835 | A1 | 10/2009 | Lysobey et al. |
| 2013/0126021 | A1 | 5/2013 | Hobbs |
| 2014/0166562 | A1 | 6/2014 | Michienzi et al. |
| 2018/0306760 | A1 | 10/2018 | Michienzi et al. |

FOREIGN PATENT DOCUMENTS

| | | |
|---|---|---|
| GB | 2431971 | 5/2007 |
| WO | 9906748 | 2/1999 |
| WO | 2005087340 | 9/2005 |
| WO | 2006091952 | 8/2006 |
| WO | 2009088663 A1 | 7/2009 |
| WO | 2013032832 A1 | 3/2013 |
| WO | 2013032833 A1 | 3/2013 |
| WO | 2013072755 | 5/2013 |
| WO | 2013113386 | 8/2013 |

OTHER PUBLICATIONS

Extended European Search Report in related European Patent Application No. 12826799.4, dated Feb. 27, 1015; 10 pages.
Kortmann, et al., "A rapid, reliable, and automatable lab-on-a-chip interface", Lab on a Chip, Mar. 3, 2009, pp. 1455-1460, vol. 9, The Royal Society of Chemistry.
International Preliminary Report on Patentability in counterpart international patent application No. PCT/US12/51974, dated Mar. 13, 2014; 7 pages.
International Search Report & Written Opinion in related international patent application No. PCT/US12/51972, dated Jan. 23, 2013; 7 pages.
International Preliminary Report on Patentability in related international patent application No. PCT/US12/51972, dated Mar. 13, 2014; 6 pages.
Extended European Search Report in related European Patent Application No. 12828910.5, dated Mar. 19, 2015; 7 pages.
Non-Final Office Action in related U.S. Appl. No. 14/238,278, dated Mar. 23, 2016; 21 pages.
Final Office Action in related U.S. Appl. No. 14/238,278, dated Jul. 27, 2016; 20 pages.
Final Office Action in related U.S. Appl. No. 14/238,278, dated May 3, 2017; 30 pages.
Non-Final Office Action in related U.S. Appl. No. 14/238,278, dated Dec. 23, 2016; 30 pages.
Examination Report in European Patent Application No. 12826799. 4, dated Apr. 11, 2017; 9 pages.
Notice of Allowance in related U.S. Appl. No. 14/238,278, dated Jan. 31, 2018.
Non-Final Office Action in related U.S. Appl. No. 14/238,278, dated Sep. 6, 2017; 27 pages.

* cited by examiner

LIQUID CHROMATOGRAPHY CONDUIT ASSEMBLIES HAVING HIGH PRESSURE SEALS

RELATED APPLICATIONS

This application claims the benefit of the earlier filing date of U.S. Provisional Patent Application Ser. No. 61/527,638, filed Aug. 26, 2011 and titled "Reusable Fitting for Attaching a Conduit to a Port," U.S. Provisional Patent Application Ser. No. 61/527,639, filed Aug. 26, 2011 and titled "Chromatography Apparatus with Diffusion-Bonded Coupler," U.S. Provisional Patent Application Ser. No. 61/527,747, filed Aug. 26, 2011 and titled "Liquid-Chromatography Conduit Assemblies Having High-Pressure Seals," U.S. Provisional Patent Application Ser. No. 61/527,648, filed Aug. 26, 2011 and titled "Electrospray Assembly for a Microfluidic Chromatography Apparatus," and U.S. Provisional Patent Application Ser. No. 61/621,852, filed Apr. 9, 2012 and titled "Chromatography Column Assembly," the entireties of which are incorporated herein by reference.

FIELD OF THE INVENTION

The invention relates generally to chromatography apparatus for operating at high pressure. More particularly, the invention relates to assemblies that include conduits terminated or joined in a manner to achieve high pressure seals.

BACKGROUND

Various types or forms of conduits, such as tubes, columns and linear flow cells are used in analytical instrumentation for transporting and/or processing fluids and samples. For example, chemical analysis instruments that utilize liquid chromatography (LC), high performance liquid chromatography (HPLC), capillary electrophoresis (CE) or capillary electro-chromatography (CEC) perform separation of a sample as the mobile phase containing the sample passes through a separation column, or concentrate a sample in a trap column before delivery of the concentrated sample to a separation column. For example, when a LC system is coupled to a light detector, linear tubes or flow cells are used to contain a fluid for optical analysis. Moreover, when a capillary LC system is interfaced to a mass spectrometer (MS), such as an electrospray ionization mass spectrometer (ESI-MS) instrument, a liquid sample processed by LC is typically pumped through a conduit to an electrospray tip. A high voltage is applied to the tip so that the liquid sample is transformed into charged particles for mass spectroscopic analysis.

Tubing used in analytical apparatus is required to withstand pressures encountered during fabrication and operation. Moreover, the tubing should be reliable for repeated use and have physical and chemical compatibility with process and sample compounds. Generally, tubing material should not corrode or leach, and sample compounds should not adhere to the tubing unless such compounds are required for a separation process.

For high pressure applications, such as HPLC applications, the tubing is typically made from stainless steel or fused silica to provide suitable strength and cleanliness. Fused-silica tubes are commonly used in capillary chromatographic systems due to desirable features. For example, the dimensions of fused silica tubing can be easily controlled during manufacturing. In addition, the wall of fused-silica tubing is clean, non-reactive and smooth, thus providing good transport of small volumes of fluids. A significant disadvantage of fused silica tubing is its vulnerability to fracturing and breaking.

Typically, tubing must be compatible with connectors which provide fluidic connections to various apparatus components. Problems associated with the use of connectors are particularly prominent for high-pressure fabrication and operation, for example, pressures in a range of 10,000 to 18,000 pounds per square inch (psi), as connectors can be the source of fluid leaks. Tubing connections should also minimize void volume, especially for systems having reduced tubing and component dimensions.

SUMMARY

In one aspect, the invention features a method of making a tubing assembly. An inner tube is inserted into an intermediate tube comprising a polymeric material. The intermediate tube is inserted into an outer tube comprising a metallic material. A collet at a longitudinal location on the outer tube is compressed to deform the outer tube and form a uniform radial crimp at the longitudinal location, thereby pressing the intermediate tube against the inner tube and generating a fluid-tight radial seal between the inner, intermediate and outer tubes.

In another aspect, the invention features a tubing assembly that includes an outer tube comprising a metal and an intermediate tube comprising a polymeric material and disposed within the outer tube. The tubing assembly also includes an inner tube disposed within the intermediate tube. The outer tube is deformed by a uniform radial crimp at a longitudinal location along the outer tube to form a fluid-tight seal between the inner, intermediate and outer tubes. The uniform radial crimp has a base region in which a diameter of the outer tube is reduced for a non-zero longitudinal length.

In yet another aspect, the invention features a chromatographic apparatus that includes a tubing assembly and a spring. The tubing assembly includes a metallic sleeve, a polymeric intermediate tube disposed in the metallic sleeve, and an inner tube disposed in the polymeric intermediate tube and having a distal end that extends beyond a distal end of the metallic sleeve. The metallic sleeve, polymeric intermediate tube and inner tube each have a proximal end that is substantially flush with the other proximal ends and configured for contacting a substrate. A portion of the metallic sleeve that extends from the proximal end is deformed in a uniform radial crimp to apply a pressure to the polymeric intermediate tube and inner tube and thereby prevents leakage along the tubing assembly. The spring is in communication with the distal end of the metallic sleeve so that the tubing assembly is urged toward an orifice in the substrate.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The term "sample", as used herein, refers to compositions of matter for which further information is desired. By way of example, the term is used to denote one or more compounds which may be of interest as to their presence or absence, concentration and/or form.

The term "capillary", as used herein, refers to tubes having an inner diameter of no greater than about 500 μm. Depending on context, the words "capillary" and "conduit" are used interchangeably herein.

The term "connector", as used herein, refers to any object or mechanism, or part of an object or mechanism, which joins pieces together or connects one mechanical part to another, such as fittings, unions, tees and couplers.

The term "light detector", as used herein, refers to any device responsive to light energy or optical radiation, or capable of determining the intensity of light that is incident on the device. By way of examples, a light detection instrument can be an ultraviolet (UV) detector, an infrared (IR) detector or a UV-visible detector.

As used herein, the words "crimping" refers to the joining of two or more malleable materials, such as metals, by deforming one or both materials to secure the materials to each other. The word "crimp" refers to the deformity or bend in one or more of the materials caused by the crimping process.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview, the invention relates to a tubing assembly, such as a tubing assembly in a chromatographic apparatus, that includes a permanently deformable outer tube, an intermediate tube and an inner tube. A radial seal is provided, for example, through one or more uniform radial crimps at one or more longitudinal locations on the tubing assembly. In some embodiments at least one end of the assembly has a uniform radial crimp and is polished so that two or more of the tubes are substantially flush with each other at the end to thereby block the passage of fluids between the ends of the tubes. In other embodiments the uniform radial crimps are at longitudinal locations where a high pressure seal is required to block the passage of fluids according to particular application requirements. Examples of longitudinal locations for uniform radial crimps include transition locations where tubes inside the assembly abut each other. The length and depth of each crimp can be formed to accommodate the requirements of the particular application. A "uniform radial crimp", as used herein, refers to a crimp formed by a compression force that is applied equally in all radial directions, that is, equally over 360° around a circumference of a tube or tubing assembly. Thus leakage along the tubing assembly is prevented and void volume is reduced or eliminated.

Advantageously, no external ferrule or ferrule swaging mechanism is needed. The uniform radial crimps are not formed using conventional ferrules which would result in single narrow line crimps having minimal longitudinal length and a crimp depth that is difficult to control. Moreover, unlike various high pressure seal tubing assemblies known in the prior art, tubing assemblies fabricated according to the present invention do not include ferrules and therefore the assemblies are more compact. The uniform radial crimps present in the various embodiments of tubing assemblies disclosed herein are accurately shaped and include a base region where the diameter of the outer tube is reduced to a smaller diameter value for an extended (i.e., non-zero) longitudinal length. By way of examples, the longitudinal length may be less than 1.0 mm or greater than 6 mm.

Figure 1A:
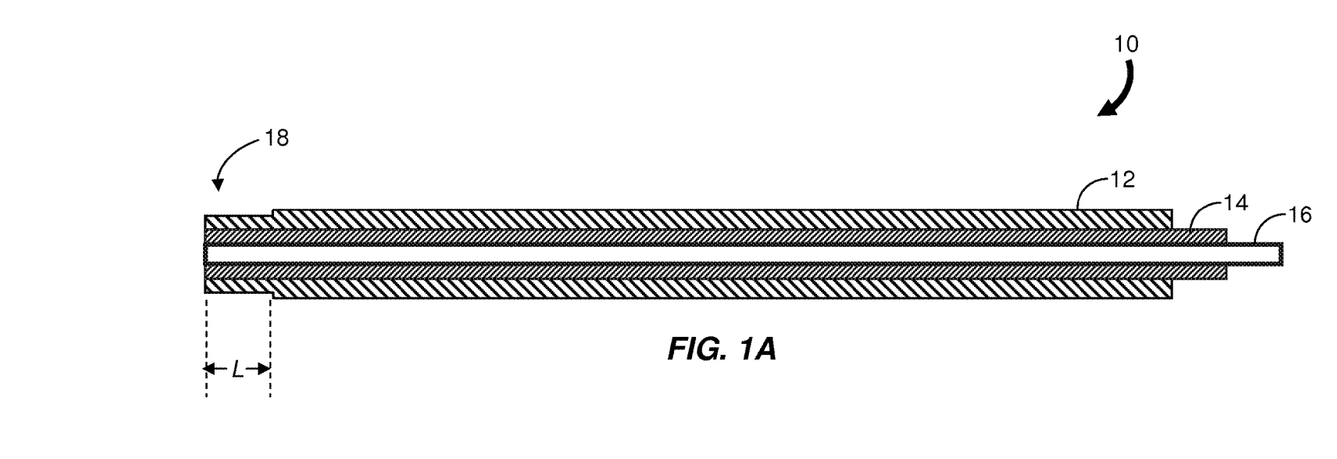
FIG. 1A is a cross-sectional diagram of an embodiment of a tubing assembly in accordance with the invention.
Figure 1B:
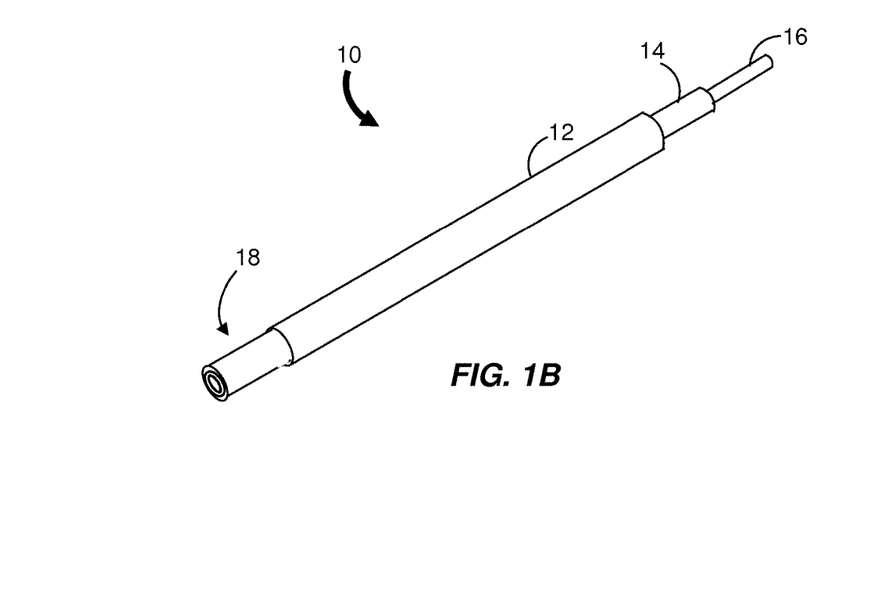
FIG. 1B is a three-dimensional view of the tubing assembly of FIG. 1A.

FIG. 1A and FIG. 1B are a cross-sectional diagram and a three-dimensional view of a tubing assembly 10 in accordance with one embodiment of the invention. The assembly 10 includes an outer tube 12, an intermediate tube 14 disposed within the outer tube 12 and an inner tube 16 disposed within the intermediate tube 14. A radial seal between the tubes 12, 14, 16 is formed by deforming the outer tube 12 to press the intermediate tube 14 against the inner tube 16 to achieve a uniform radial crimp 18 at an end of the tubing assembly 10. The longitudinal length L and depth of the uniform radial crimp 18 can be selected according to the requirements of a particular application. The radial seal formed by this process can withstand pressures that can exceed 18,000 psi. In some embodiments, two or more uniform radial crimps are formed at different longitudinal locations along the tubing assembly 10 with one of the crimps formed at an end of the tubing assembly 10.

In some embodiments of a method of making a tubing assembly, the uniform radial crimp 18 is produced by a pneumatic or hydraulic collet having a circular bore. The collet is machined to produce the desired length, diameter, and shape of crimp, then is positioned to encircle an end of the tubing assembly 10 and is compressed uniformly around the tubing assembly 10.

Figure 1C:
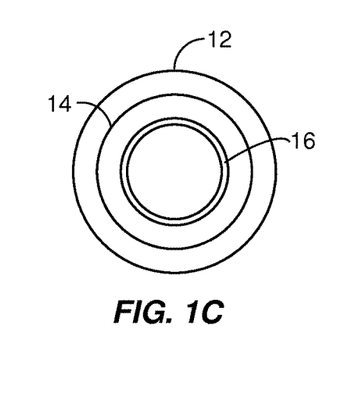
FIG. 1C is a view of the proximal end of the tubing assembly of FIG. 1A.

The proximal end (having the crimp 18) of the tubing assembly 10 is polished such that the outer, intermediate and inner tubes 12, 14, 16 all terminate in a plane that is perpendicular to a longitudinal axis of the tubing assembly 10 as shown in FIG. 1C. In some implementations, more than one crimp is formed at the polished end to consolidate a fluid-tight seal along the tubing assembly 10.

In alternative embodiments, one or both ends of the tubing assembly are trimmed or shaped to be compatible with other fluidic components, such as connectors, which, for example, mate with large diameter metallic tubing to obtain substantially fluid-tight and durable plumbing connections at pressures up to 18,000 psi or greater.

The inner tube may be implemented as a chromatography column, such as an analytical column or a trap column. In such embodiments, one or more frits are optionally provided at one or both ends of the inner tube to help retain a packing material in the column without substantial increase of void volume. The fritted end of the tube is optionally heated to sinter the packing material. Upon completion of the frit, the remaining unpacked space of the tube may be filled with packing material. For example, a frit can be formed from a siloxane-based thermoset polymer such as poly dimethyl siloxane ("PDMS").

The outer, intermediate, and inner tubes 12, 14, 16 are each fabricated in any desired dimensions in any suitable manner from any suitable materials. For example, the inner tube 16 can be formed of stainless steel or, more commonly, fused silica. The intermediate tube 14 can be formed of a polymeric material, for example, VICTREX® PEEK polymer available from Victrex PLC, Lancashire, United Kingdom, TEFLON® polymer available from Dupont Corporation, Delaware, USA or PEEKsil™ polymer available from SGE Analytical Science, Pty Ltd, Victoria, Australia. The outer tube 12 is formed of a metallic material, for example, hardened or annealed steel. A hardened steel reduces the occurrences of accidental bending.

In one particular example, a completed tubing assembly includes an inner tube 16 having an inner diameter (ID) of about 30 μm and an outer diameter (OD) of about 360 μm. The intermediate tube 14 has an ID of about 380 μm, which is slightly greater than the OD of the inner tube 16, and an OD of about 760 μm. The outer tube 12 has an OD slightly greater than about 1000 μm. The ID of the outer tube 12 is selected to be compatible with the OD of the intermediate tube 14, that is, to be slightly greater than about 760 μm. Thus the inner tube 16 can be inserted into the intermediate tube 14 and the intermediate tube 14 can be inserted into the outer tube 12. Preferably, during insertion, there is some contact between the circumference of the intermediate tube 14 and the inner circumference of the outer tube 12. It should be appreciated that this example is merely illustrative and non-limiting.

Figure 2A:
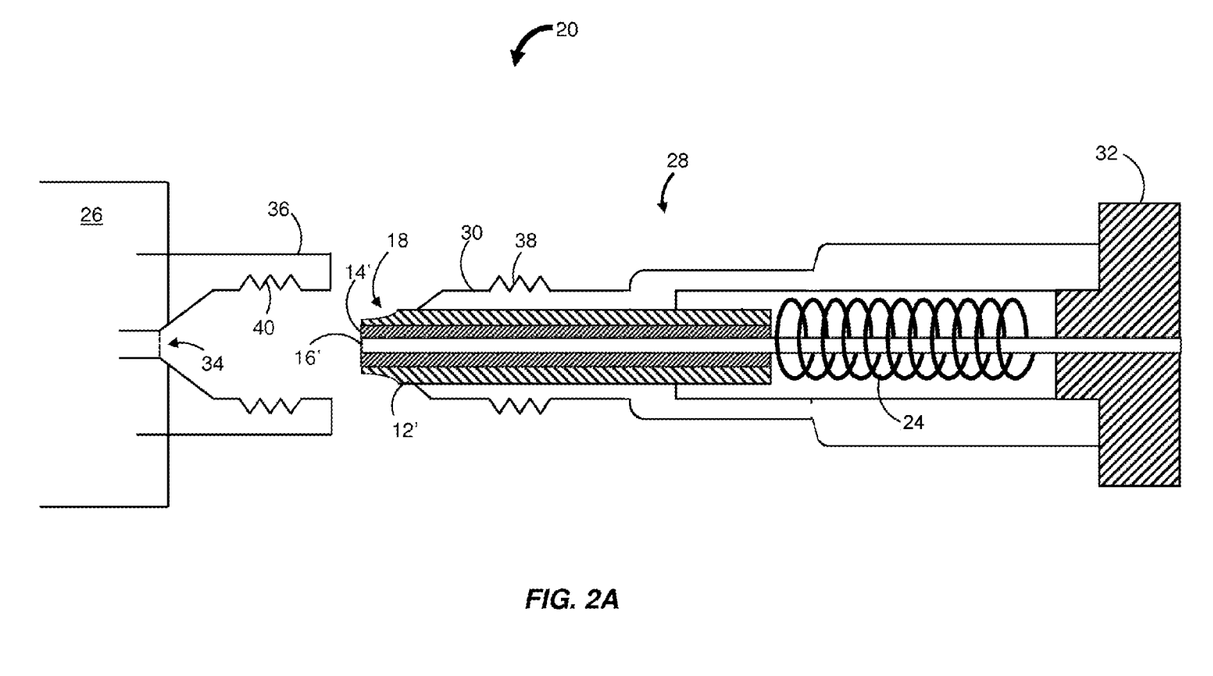
FIG. 2A is a cross-sectional diagram of a portion of an embodiment of a chromatographic apparatus in accordance with the invention.

FIG. 2A is a cross-sectional diagram of a portion of one embodiment of a chromatographic apparatus 20 in accordance with the invention. The chromatographic apparatus 20 includes a tubing assembly, a spring 24 and a substrate or chromatographic processing unit 26. The tubing assembly is similar to the tubing assembly 10 of FIG. 1A and includes a metallic outer tube (i.e., sleeve) 12', a polymeric intermediate tube 14' and an inner tube 16'.

The spring 24 is enclosed in a fitting 28 having a ferrule 30 and a cap 32. The illustrated spring 24 is in the form of a helical coil; however, more generally, the spring can be any elastic device that can be disposed within the fitting 28 and which exerts a force when under compression. Preferably, the sleeve is formed of a hardened steel and the ferrule 30 is formed of PEEK which is capable of operation at high pressures and enables the fitting 28 to be used more than once. The substrate 26 defines one or more columns, for example, trap columns and/or analytical columns (not shown), which are in fluid communication with each other and with an outlet port 34 within a coupling body 36 which may be formed, for example, of a metal or a plastic.

The distal end (not shown) of the inner tube 16' extends beyond the distal end of the metallic sleeve 12' to join other fluidic components or connections. The proximal ends of the sleeve 12', intermediate tube 14' and inner tube 16' are substantially flush with each other and are adapted to abut the outlet 34 of the substrate 26. A portion of the sleeve 12' at the proximal end is substantially uniformly crimped 18 to form a fluid-tight seal between the inner and intermediate tubes 16' and 14', and to prevent leakage along the tubing assembly. The fitting 28 includes a threaded exterior surface 38 that engages a threaded interior surface 40 of the coupling body 36. When the fitting 28 fully engages the coupling body 36, a spring force generated by the spring 24 urges the tubing assembly toward the outlet port 34. The chromatographic apparatus 20 provides a fluid-tight seal and a substantially zero void volume at the outlet 34 of the substrate 26 and can operate under high pressures that can exceed 10,000 psi.

Figure 2B:
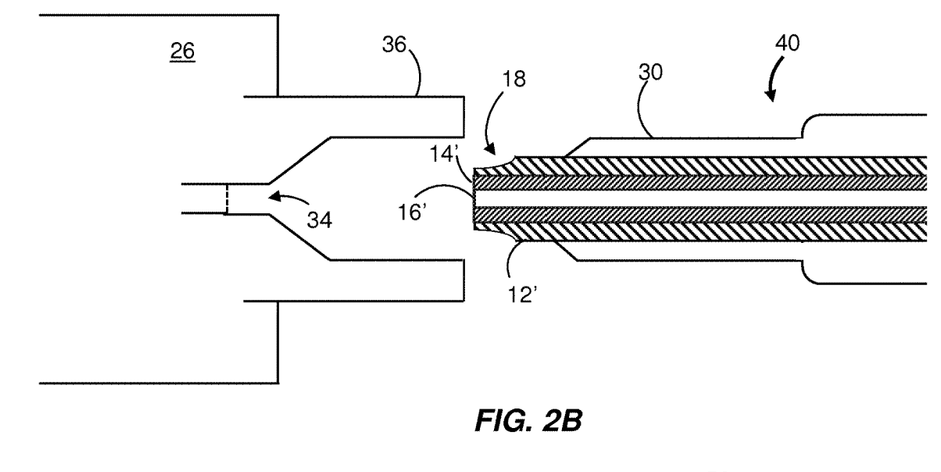
FIG. 2B is a cross-sectional diagram of another embodiment of a chromatographic apparatus in accordance with the invention.

FIG. 2B shows an alternative embodiment in which a fitting 40 without any threads is used to achieve a fluidic coupling at the outlet port 34 of the substrate 26. In other embodiments, the fitting 30 or 40 can be used to couple to a fluidic inlet. A fluidic port can be, by way of examples, an output port of a pump, an input port of a column, a sample injector port, a port of a valve or a port of a flow splitter tee.

In some embodiments, the apparatus 20 is a HPLC system or a UHPLC system, such as a modified ACQUITY® UPLC® system or nanoACQUITY® UPLC® system available from Waters Corporation, Milford, Mass.

In view of the above description, one having ordinary skill in the separation arts will understand that tubing assemblies are optionally used in conjunction with any suitable connectors, including known connectors. One suitable commercially available connector, which includes a fitting body, ferrule, and compression screw, is the SLIPFREE™ connector available from Waters Corporation, Milford, Mass. Other suitable connectors utilize a two-ferrule system. Such connectors have applications, for example, in high-pressure environments that may exceed 18,000 psi.

Figure 3:
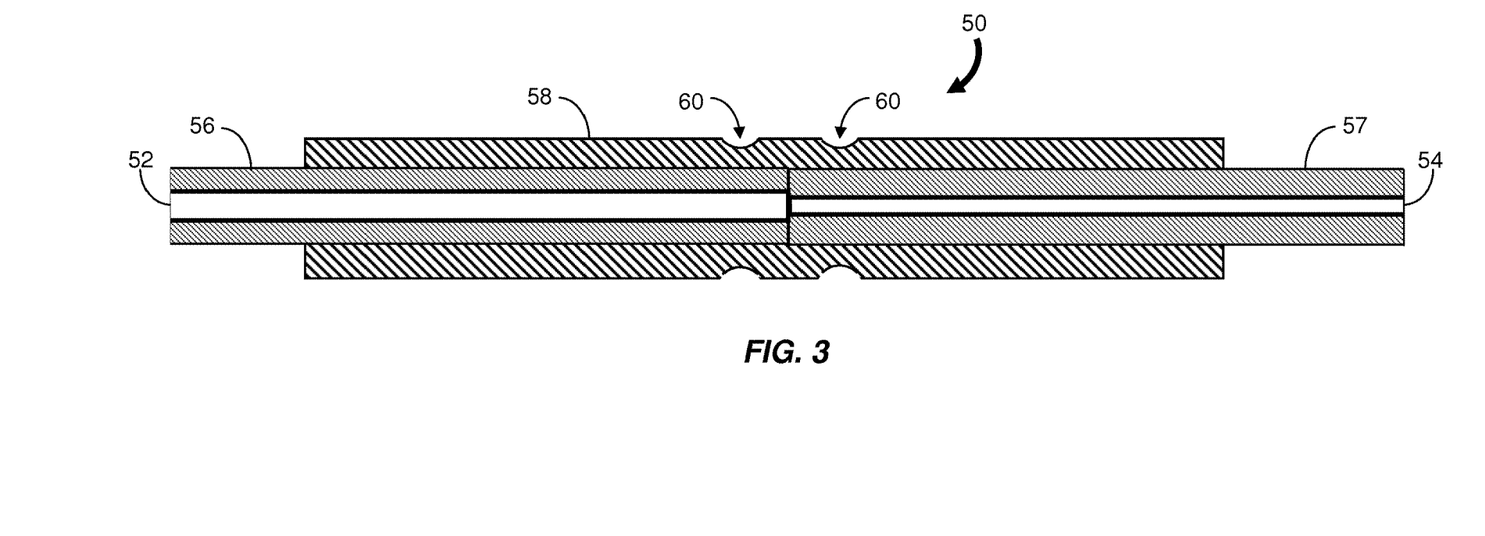
FIG. 3 is a cross-sectional diagram of another embodiment of a tubing assembly in accordance with the invention.

FIG. 3 is a cross-sectional diagram of an embodiment of a tubing assembly 50 having two inner tubes 52 and 54 of different inner and outer diameters joined to each other in accordance with the invention. The two inner tubes 52, 54 are disposed within respective intermediate tubes 56 and 57 so that the end faces of the inner tubes 52, 54 abut each other to define an interface having substantially zero void volume. In some implementations, the narrower inner tube 52 is inserted into one end of the intermediate tube 56 and the larger inner tube 54 is inserted into the opposite end of the intermediate tube 56 until the end faces of the inner tubes 52, 54 are in contact. The intermediate tube 56 is then inserted into a steel outer tube 58 to complete the formation of the tubing assembly 50. In an alternative embodiment, the outer diameters of the two inner tubes 52, 54 are the same, allowing a single intermediate tube to be used.

A radial seal between the inner, intermediate and outer tubes 52, 54, 56, 57, 58 is formed by deforming the outer tube 58 to thereby press the intermediate tubes 56 against the inner tubes 52, 54 with at least two uniform radial crimps 60, one at each side of the abutment of the inner tubes 52, 54.

In some embodiments in which multiple inner tubes are provided, multiple crimps are applied such that at least one crimp is formed along the assembly at a location of each inner tube. The length and depth of each crimp can be varied according to the application. In other embodiments, an inner tube can be mated to a second inner tube that has no lumen. For example, the second inner tube can be an optical fiber (i.e., an "optical conduit").

The tubing assembly 50 acts as a union for connecting two similar or dissimilar inner tubes. Thus, the need for conventional unions for the connection can be avoided while a fluid-tight seal and substantially zero void volume connection are realized. Moreover, the assembly 50 remains stable over repeated high-pressure cycling.

Figure 4A:
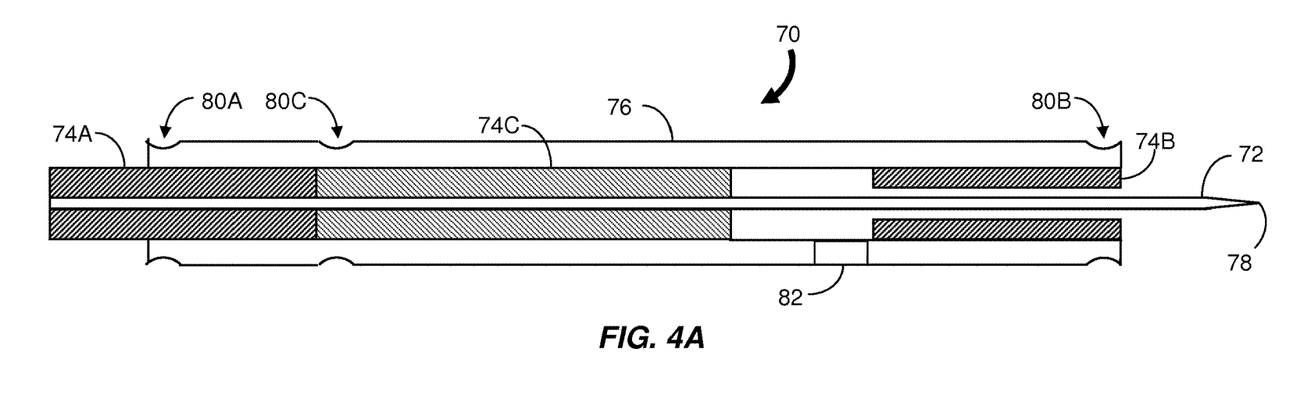
FIG. 4A is a cross-sectional diagram of an embodiment of an emitter tubing assembly in accordance with the invention.

FIG. 4A is a cross-sectional diagram of an embodiment of an emitter tubing assembly 70 in accordance with the invention. The emitter tubing assembly 70 includes an emitter 72, three intermediate tubes 74A, 74B and 74C (generally 74) and an outer tube 76 within which the three intermediate tubes 74 are disposed. The emitter 72 is equipped with an electrospray tip 78 at one end which is configured to interface with an inlet port of an ESI-MS instrument. The opposite end of the emitter tubing assembly 70 is configured to couple to an outlet port of a chromatographic processing unit.

A radial seal is formed between the emitter 72, the intermediate tubes 74 and the outer tube 76 via three uniform radial crimps 80A, 80B and 80C (generally 80). The crimps 80A and 80B are formed at the two ends of the emitter tubing assembly 70. The crimp 80C is formed at a longitudinal position along the assembly 70 where the intermediate tube 74B is located underneath. In some embodiments, the crimps 80A and 80B are produced by a pneumatic or hydraulic collet having a machined circular bore. During the process, each collet is longitudinally positioned to encircle a portion of the emitter tubing assembly 70 and is compressed uniformly via application of a gas pressure in a range of about 2,000 psi to about 3,000 psi. The crimp 80C is formed by crimping a fitting disposed around the emitter tubing assembly 70 to deform the outer tube 76 to seal the intermediate tube 74C against the emitter 72.

The end of the emitter tubing assembly 70 near the electrospray tip 78 includes a gas passageway for receiving and delivering a nebulizer gas to the electrospray tip 78 to nebulize a liquid sample and dry the droplets. The gas passageway includes the gap between the intermediate tube 74B and the emitter 72. The gap is sized to achieve a desired flow rate for the nebulizer gas and to avoid improper divergence of the gas at the electrospray tip 78. A gas inlet port 82 on the outer tube 76 provides a means to externally supply the nebulizer gas to the gas passageway.

In the illustrated embodiment, the emitter 72 and outer tube 76 are preferably made of a metallic material, for example, stainless steel. The intermediate tubes 74A and 74B are preferably formed of a polymeric material having sufficient deformability, for example, a PEEK polymer, and the intermediate tube 74C is preferably formed of a carbon-loaded PEEK material which is electrically conductive. In other embodiments, the emitter 72 comprises a polymeric material (e.g., a hydrophobic polymer) or is coated with a hydrophobic polymer.

In the embodiment shown in FIG. 4a, the emitter 72 has an inner diameter (ID) of about 30 µm and an outer diameter (ID) of about 360 µm. The intermediate tubes 74A, 74C have an ID of about 380 µm, slightly larger than the OD of the emitter 72, and an OD of about 760 µm. The intermediate tube 74B has an ID that is slightly larger than the IDs of the other intermediate tubes 74A, 74C to establish a gap between the intermediate tube 74B and the emitter 72 to allow a nebulizer gas to flow to the electrospray tip 78. The outer tube 76 has an OD that is slightly larger than about 1000 µm and has an ID selected to be compatible with the ODs of the intermediate tubes 74.

Figure 4B:
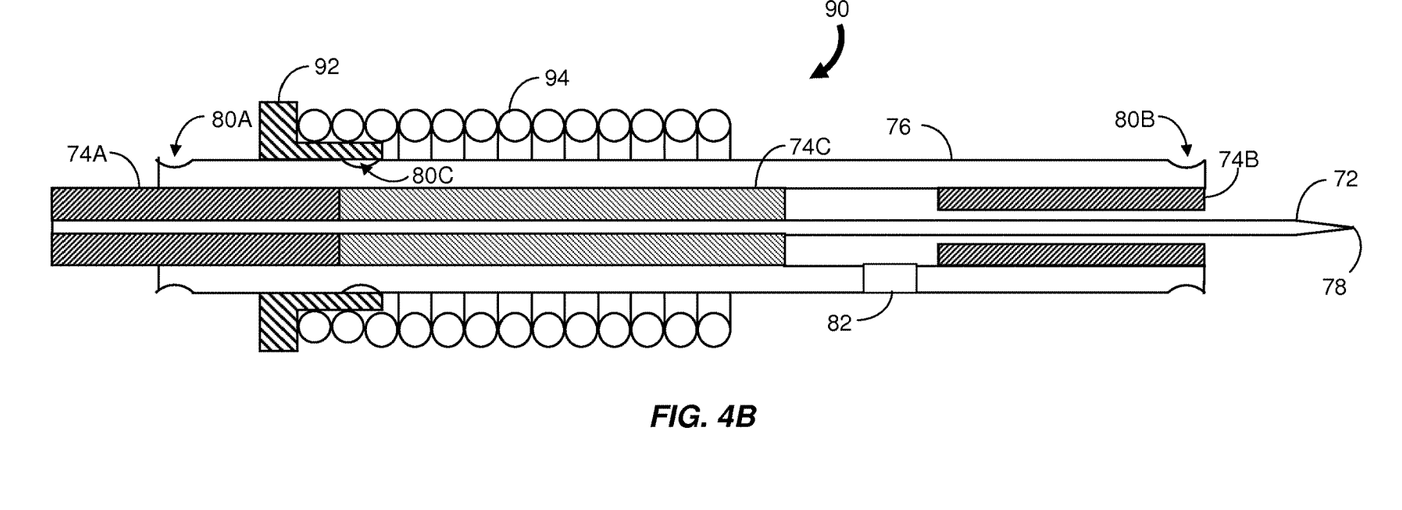
FIG. 4B is a cross-sectional diagram of another embodiment of an emitter tubing assembly in accordance with the invention.

FIG. 4B is a cross-sectional diagram of an emitter tubing assembly 90 that includes a fitting 92 disposed around one end of the assembly 90 and a spring 94 coupled to the fitting 92. The fitting 92 is preferably fixedly mounted to the outer tube 76 and the spring 94 is either fixedly or removably attached to the fitting 92, for example, by clips, magnets or threads. The fitting 92 is formed of a metallic material such as stainless steel or a polymeric material such as PEEK, and the spring 94 is preferably a metallic spring.

Figure 5:
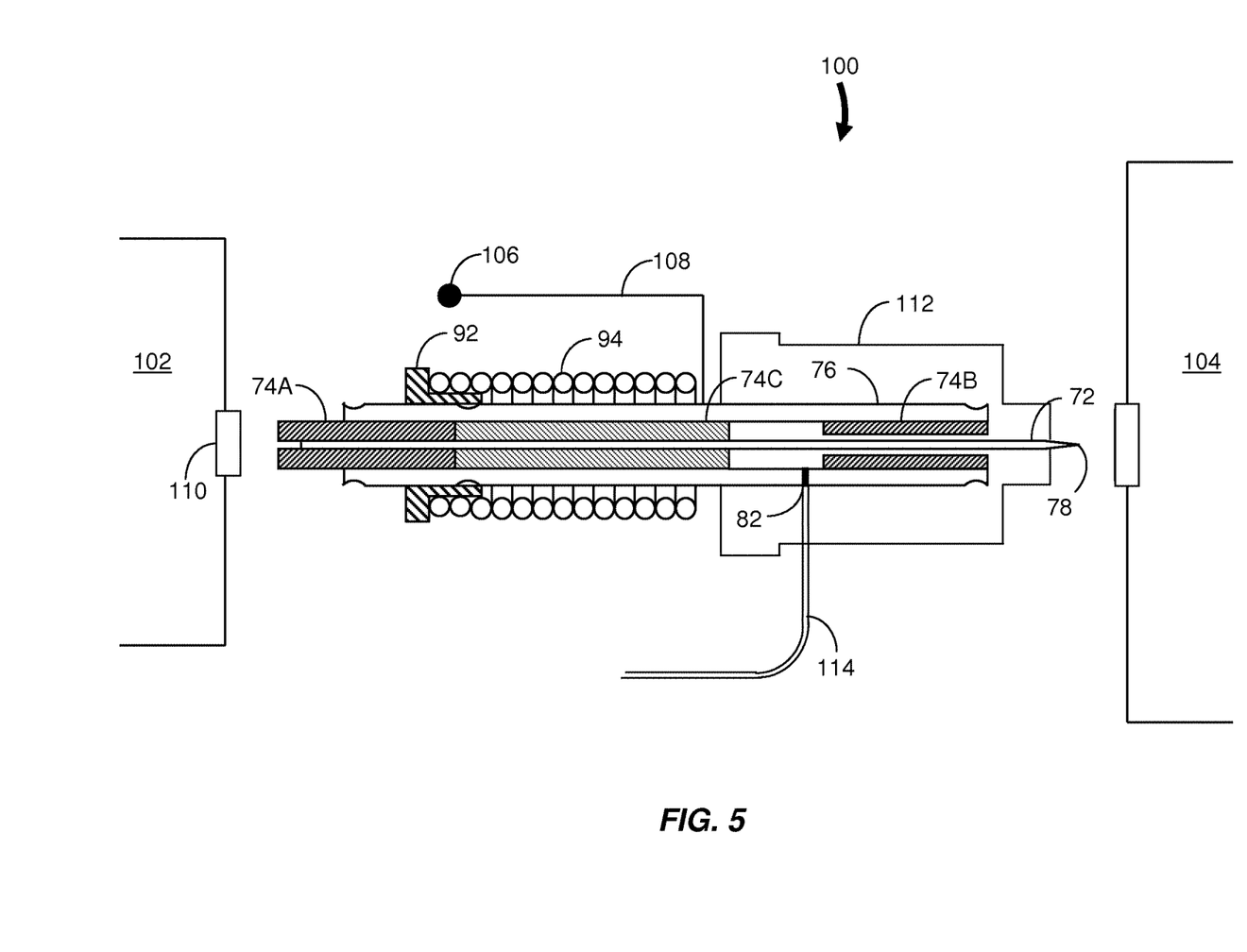
FIG. 5 is a cross-sectional diagram of a portion of an embodiment of a chromatography apparatus in accordance with the invention.

FIG. 5 is a cross-sectional diagram of a portion of an embodiment of a chromatography apparatus 100 in accordance with principles of the invention. The apparatus 100 includes the emitter tubing assembly 90 of FIG. 4B, a chromatographic processing unit 102, for example, such as the processing unit 26 of FIG. 2A, and an EMI-MS unit 104. Eluent from the chromatographic processing unit 102 is passed to the emitter tubing assembly and the nebulized eluent from the electrospray tip 78 is provided to the EMI-MS unit 104.

The end of the emitter tubing assembly nearest the electrospray tip 78 is part of an electrical circuit. A high voltage of approximately 3 kV generated by a power supply (not shown) is applied by a high voltage input terminal 106 and cable 108 to the emitter 72 by way of intervening elements. More specifically, the intervening elements can be the metallic spring 94, metallic fitting 92, outer tube 76 and electrically conductive intermediate tube 74C.

The end of the emitter tubing assembly opposite to the electrospray tip 78 includes a protrusion of the intermediate tube 74A formed of a deformable PEEK material. The fitting 92, when receiving a spring force from the spring 94, urges the emitter tubing assembly toward an outlet 110 of the chromatographic processing unit 102. The protruding intermediate tube 74A fits into the outlet 110 to form a fluid-tight seal while preventing the emitter 72 from coming into direct contact with the relatively rigid outlet 110. The resulting coupling maintains a fluidic passageway with substantially no void volume at the interface.

The end of the emitter tubing assembly having the electrospray tip 78 is enclosed in a stainless steel block 112. A gas tube or channel 114 passes through the block 112 and allows the gas inlet port 82 to be coupled to a source of nebulizer gas. A gap (not shown) may be provided between the outer tube 76 and the block 112 to vent excessive nebulizer gas from the apparatus 100.

In a non-limiting numerical example for the illustrated embodiment, the emitter 72 has an ID of about 30 µm and an OD of about 360 µm. The intermediate tubes 74 have an ID larger than the OD of the emitter 72, for example, an ID of about 380 µm and an OD of about 760 µm. The outer tube 76 has an OD of slightly larger than about 1,000 µm and an ID selected to be compatible with the OD of the intermediate tubes 74.

Figure 6:
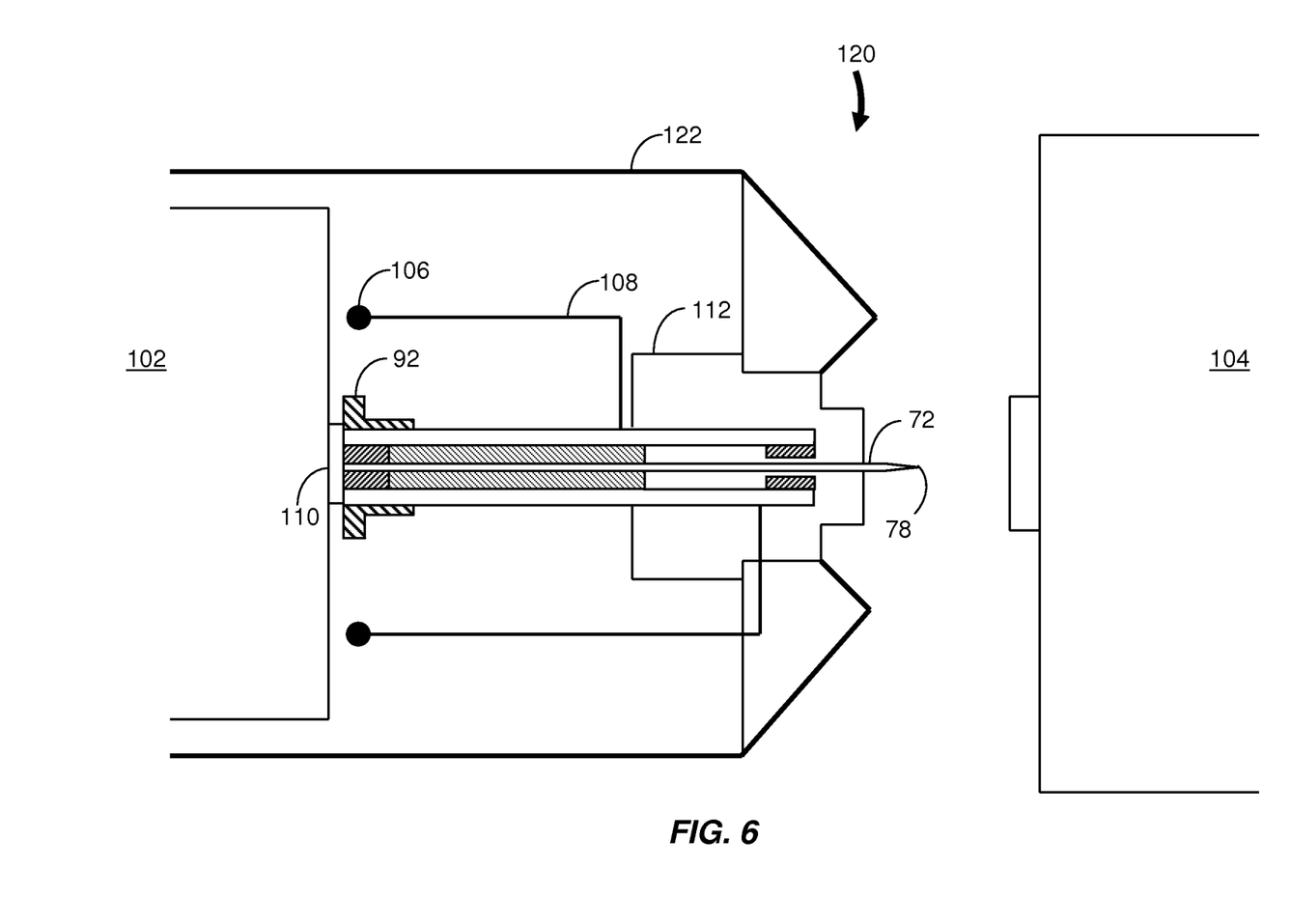
FIG. 6 is a cross-sectional diagram of a portion of another embodiment of a chromatographic apparatus in accordance with the invention.

FIG. 6 is a cross-sectional diagram of a portion of an apparatus 120 in accordance with another embodiment in which a chromatographic processing unit 102 and an emitter tubing assembly are both installed within a microfluidic cartridge 122 which interfaces directly with an ESI-MS unit 104. The microfluidic cartridge 122 can include additional components (not shown), such as temperature control elements for heating and cooling the chromatographic processing unit 102, internal circuitry for supporting signal communications with external devices, and connectors (e.g., springs and mechanical fasteners) for joining the chromatographic processing unit 102 and the stainless steel block 112. The microfluidic cartridge 122 also includes windows or apertures through which external components and devices, such as a high voltage power supply and a nebulizer gas line, are connected to corresponding internal circuitry and structure. Various forms of the microfluidic cartridge 122 are described in PCT Patent Publication No. WO 2010/102194 A1 which is incorporated herein by reference.

Figure 7:
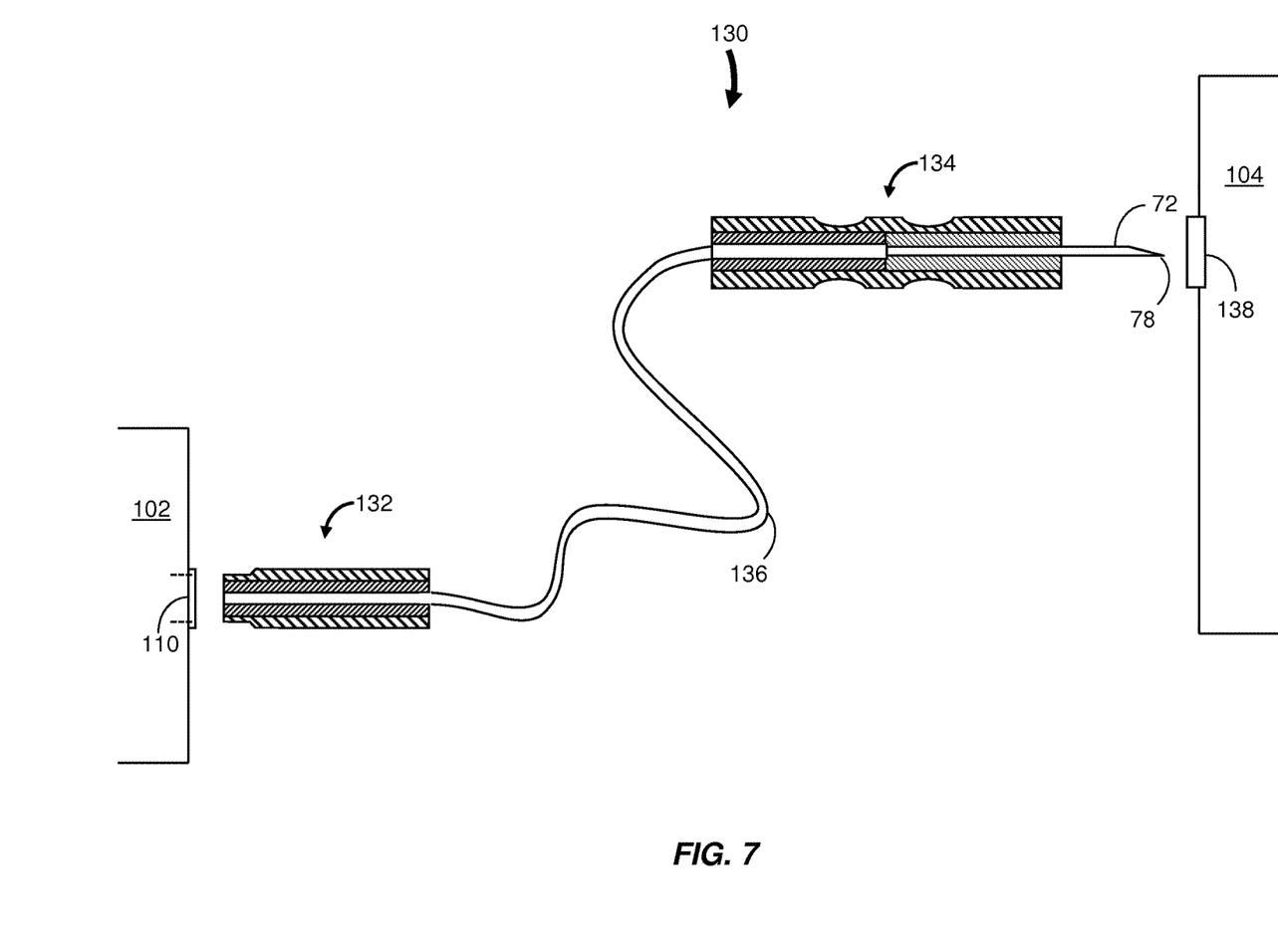
FIG. 7 is a cross-sectional diagram of a portion of another embodiment of a chromatographic apparatus in accordance with the invention.

In the embodiments illustrated in FIG. 5 and FIG. 6, the emitter 72 embedded in the emitter tubing assembly 70 interfaces directly with the chromatographic processing unit 102 and the ESI-MS unit 104; however, in a preferred embodiment shown in the cross-sectional diagram of FIG. 7, the emitter 72 interfaces directly with the ESI-MS 104 without having a direct interface to the chromatographic processing unit 102. The apparatus 130 includes a first tubing assembly 132 in fluid communication with the chromatographic processing unit 102, a second tubing assembly 134 in communication with the EMI-MS unit 104, and a capillary 136 to conduct fluid from the first tubing assembly 132 to the second tubing assembly 134.

The first tubing assembly 132 is similar to the tubing assembly 10 of FIG. 1A and the second tubing assembly is similar to the tubing assembly 50 of FIG. 3. The first tubing assembly 132 is configured to engage the chromatographic processing unit 102 at its outlet 110. The second tubing assembly 134 is configured to enable the electrospray tip 78 at the end of the emitter 72 to be disposed within an inlet port 138 of the ESI-MS unit 104. In addition, the second tubing assembly 134 includes components (not shown) that may interface with the ESI-MS unit 104 to enable a high voltage to be applied to the emitter 72 and to support nebulizer gas flow. The capillary 136 is coupled at its ends to the first and second tubing assemblies 132, 134 to permit the outlet 110 of the chromatographic processing unit 102 to be in fluid communication with the emitter 72. Thus a liquid sample processed by the chromatographic processing unit 102 flows through the capillary 136 to the emitter 72 and a continuous mist of charged droplets is discharged from the emitter tip 78. The electric repulsion between the charged droplets during evaporation results in an aerosol cloud of small charged particles that are provided to the ESI-MS unit 104.

Figure 8A:
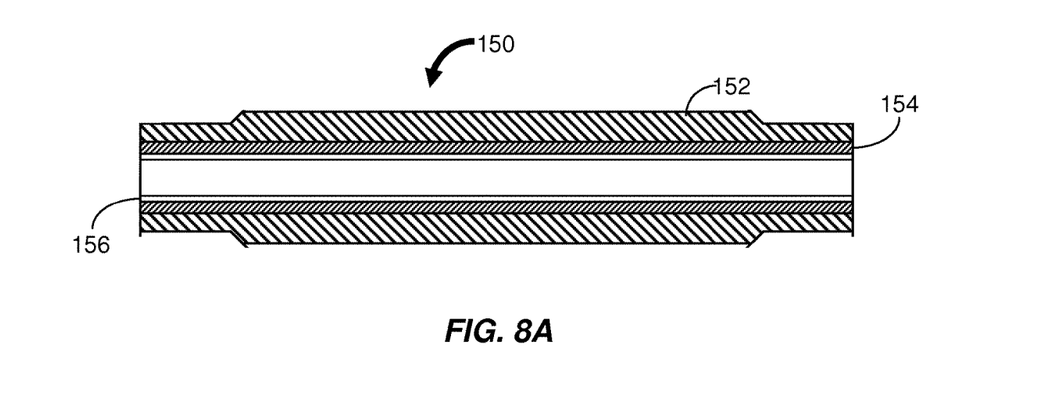
FIG. 8A is a side cross-sectional view of another embodiment of a chromatographic apparatus according to principles of the invention.
Figure 8B:
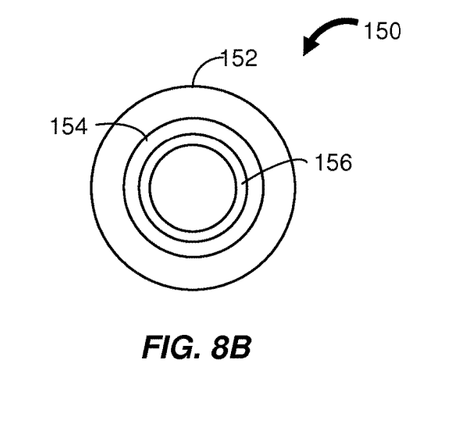
FIG. 8B is an end cross-sectional view of the chromatographic apparatus of FIG. 8A.

FIG. 8A and FIG. 8B show side and end cross-sectional views, respectively, of another embodiment of a chromatographic apparatus 150 according to principles of the invention. The apparatus 150 is a flow cell used to contain a sample solution from a chromatographic processing unit for analysis using optical techniques.

The flow cell 150 includes an outer tube 152, an intermediate tube 154 and an inner tube 156. At least one uniform radial crimp is formed at each end of the flow cell 150. The flow cell can be fluidically coupled at its ends (i.e., "ports") to permit the fluid to flow into or out from the interior of the inner tube 156. The cylindrical volume encompassed by the inner tube 156 includes the fluid to be analyzed.

The flow cell 150 is configured at one end for optical coupling to an optical source and at the other end for optical coupling to an optical detector, for example, via optical conduits such as optical fibers, optical fiber bundles, reflectors and/or other optical components. The optical energy transmitted through and/or emitted by the fluid flowing through the inner tube 156 is sensed by the optical detector.

The inner tube 156 is formed of any suitable materials, including, for example, one or more materials that have optical properties suited to the functioning of an optical detector for use with a flow cell. The material preferably has a refractive index that is less than the refractive index of the fluid contained within the cylindrical volume encompassed by the inner tube 156.

In one preferred embodiment, the inner tube 156 is formed of a fluoropolymer, such as TEFLON® AF amorphous fluoropolymer (available from E. I. du Pont de Nemours and Company, Wilmington, Del.). Other embodiments utilize a mixture of a polymer and particles. For example, an amorphous fluoropolymer can be mixed with particles, such as carbon particles, that block stray light. One such suitable material is carbon-doped TEFLON AF ("black TEFLON AF"). To prepare this material, TEFLON AF resin is mixed, for example, with carbon black in a concentration range of 0.01%-0.1%.

In alternative embodiments, the inner tube 156 is a fused-silica capillary having an outer surface that is coated with a material having a lower refractive index. In still another example, the inner tube 156 has a high reflectivity interior cylindrical surface.

While the invention has been shown and described with reference to specific embodiments, it should be understood by those skilled in the art that various changes in form and detail may be made therein without departing from the spirit and scope of the invention as recited in the accompanying claims. For example, the tubing assembly described above can also be utilized to deliver slurry to pack a column in a microfluidic substrate. Moreover, a tubing assembly optionally includes two or more conduit interfaces, and the associated conduits may have two or more different inner diameters or different lumen shapes.

What is claimed is:

1. A liquid chromatography tubing assembly comprising:
 an outer tube comprising a metal;
 an intermediate tube comprising a polymeric material and disposed within the outer tube; and
 first inner tube disposed within the intermediate tube, wherein the outer tube is deformed by a uniform radial crimp at a longitudinal location along the outer tube to form a fluid-tight seal between the first inner, intermediate and outer tubes, and wherein the uniform radial crimp has a base region over which a diameter of the outer tube is reduced for a longitudinal length greater than 6 mm.

2. The liquid chromatography tubing assembly of claim 1 further comprising a second inner tube disposed in the intermediate tube.

3. The liquid chromatography tubing assembly of claim 2, wherein the first inner tube has an inner diameter that is different from an inner diameter of the second inner tube.

4. The liquid chromatography tubing assembly of claim 1 wherein the first inner tube comprises one of steel and fused silica.

5. The liquid chromatography tubing assembly of claim 1 wherein the polymeric material comprises one of polyetheretherketone, polytetrafluoroethylene, and polyimide.

6. The liquid chromatography tubing assembly of claim 1 wherein the metal comprises one of hardened steel and annealed steel.

7. A liquid chromatography tubing assembly comprising:
an outer tube comprising a metal;
an intermediate tube comprising a polymeric material and disposed within the outer tube; and
first inner tube disposed within the intermediate tube, wherein the outer tube is deformed by a uniform radial crimp at a longitudinal location along the outer tube to form a fluid-tight seal between the first inner, intermediate and outer tubes, and wherein the uniform radial crimp has a base region over which a diameter of the outer tube is reduced for a longitudinal length greater than one millimeter.

8. The liquid chromatography tubing assembly of claim 7 further comprising a second inner tube disposed in the intermediate tube.

9. The liquid chromatography tubing assembly of claim 8, wherein the first inner tube has an inner diameter that is different from an inner diameter of the second inner tube.

10. The liquid chromatography tubing assembly of claim 7 wherein the first inner tube comprises one of steel and fused silica.

11. The liquid chromatography tubing assembly of claim 8 wherein the polymeric material comprises one of polyetheretherketone, polytetrafluoroethylene, and polyimide.

12. The liquid chromatography tubing assembly of claim 7 wherein the metal comprises one of hardened steel and annealed steel.

* * * * *